United States Patent [19]
Mrozik et al.

[11] Patent Number: 5,030,622
[45] Date of Patent: Jul. 9, 1991

[54] AVERMECTIN DERIVATIVES

[75] Inventors: Helmut Mrozik, Matawan, N.J.; Peter J. Sinclair, Suffern, N.Y.

[73] Assignee: Merck & Co., Inc., Rahway, N.J.

[21] Appl. No.: 360,620

[22] Filed: Jun. 2, 1989

[51] Int. Cl.$^5$ ...................... A61K 31/70; C07H 17/04
[52] U.S. Cl. .......................... 514/30; 536/7.1
[58] Field of Search ............... 536/7.1; 514/30

[56] References Cited

U.S. PATENT DOCUMENTS

| 4,199,569 | 4/1980 | Chabala et al. | 514/30 |
| 4,206,205 | 6/1980 | Mrozik et al. | 514/30 |
| 4,310,519 | 1/1982 | Albers-Schonberg et al. | 514/30 |
| 4,806,527 | 2/1989 | Christensen et al. | 536/7.1 X |
| 4,831,016 | 5/1989 | Mrozik et al. | 536/7.1 X |
| 4,873,224 | 10/1989 | Linn et al. | 536/7.1 X |

FOREIGN PATENT DOCUMENTS

| 214731 | 3/1987 | European Pat. Off. |
| 284176 | 1/1988 | European Pat. Off. |
| 276103 | 7/1988 | European Pat. Off. |
| 276131 | 7/1988 | European Pat. Off. |

OTHER PUBLICATIONS

Chen et al., *Absts. Pag. Am. Chem. Soc.,* 186th Mtg MBTD 28 (1983).
Schulman et al., (I) *J. Antibiotic* 38, pp. 1494–1498 (1985).
Schulman et al., (II), *Antimicrobial Agents and Chemotherapy* 31, pp. 744–747 (1987).
Davies et al., *Nat. Prod. Rep.* 3, pp. 87–121 (1986).
Streitwieser, Jr. et al., Introduction to Organic Chemistry, Second Edition, p. 804 (1981).

*Primary Examiner*—Elli Peselev
*Attorney, Agent, or Firm*—David L. Rose; Joseph F. DiPrima

[57] ABSTRACT

There are disclosed novel avermectin derivatives wherein the outer oleandrose ring of avermectin or avermectin monosaccharide is homologated by addition of diazomethane to 4''- or 4'-oxo-avermectin to afford the oleandrose 4''- or 4'-spiro-epoxide. The homologated avermectins can then be further derivatized to afford additional novel avermectins. The new compounds are potent antiparasitic agents, in particular, the compounds are anthelmintic, insecticidal and acaricidal agents.

11 Claims, No Drawings

AVERMECTIN DERIVATIVES

BACKGROUND OF THE INVENTION

The term avermectin (previously referred to as C-076) is used to describe a series of compounds isolated from the fermentation broth of an avermectin producing strain of *Streptomyces avermitilis* and derivatives thereof. The morphological characteristics of the culture are completely described in U.S. Pat. No. 4,310,519. The avermectin compounds are a series of macrolides, each of which is substituted at the 13 position with a 4-(α-L-oleandrosyl)-α-L-oleandrose group. The avermectin compounds and the instant derivatives thereof have a very high degree of anthelmintic and anti-parasitic activity. The avermectin series of compounds isolated from the fermentation broth have the following structure:

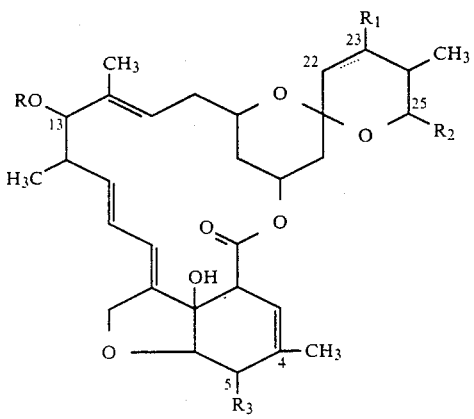

wherein R is the 4'-(α-L-oleandrosyl)-α-L-oleandrosyl group of the structure:

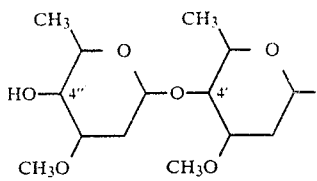

and wherein the broken line indicates a single or a double bond; $R_1$ is a hydrogen or hydroxy and is present only when said broken line indicates a single bond; $R_2$ is iso-propyl or sec-butyl; and $R_3$ is methoxy or hydroxy There are eight different avermectin natural product compounds and they are given the designations A1a, A1b, A2a, A2b, B1a, B1b, B2a, and B2b based upon the structure of the individual compounds.

In the foregoing structural formula, the individual avermectin compounds are as set forth below. (The R group is 4'-(α-L-oleandrosyl)-α-L-oleandrose):

|     | $C_{22}$-$C_{23}$ | $R_1$ | $R_2$ | $R_3$ |
| --- | --- | --- | --- | --- |
| A1a | (22,23-double bond) | — | sec-butyl | —OCH3 |
| A1b | (22,23-double bond) | — | iso-propyl | —OCH3 |
| A2a | (22,23-single bond) | OH | sec-butyl | —OCH3 |
| A2b | (22,23-single bond) | OH | iso-propyl | —OCH3 |
| B1a | (22,23-double bond) | — | sec-butyl | —OH |
| B1b | (22,23-double bond) | — | iso-propyl | —OH |
| B2a | (22,23-single bond) | OH | sec-butyl | —OH |

-continued

|     | $C_{22}$-$C_{23}$ | $R_1$ | $R_2$ | $R_3$ |
| --- | --- | --- | --- | --- |
| B2b | (22,23-single bond) | OH | iso-propyl | —OH |

The avermectin compounds are generally isolated as mixtures of a and b components. Such compounds differ only in the nature of the R2 substituent and the minor structural differences have been found to have very little effect on the isolation procedures, chemical reactivity and biological activity of such compounds.

In addition to these natural avermectins containing the 25-iso-propyl or 25-sec-butyl-substituent, closely related derivatives containing other branched or cyclic 25-alkyl or 25-alkenyl substituents, optionally further substituted by heteroatoms such as oxygen, sulfur, nitrogen, halogen and the like are known in the literature. These derivatives are obtained through various adjustments and additions to the fermentation procedures as described fully in the European Patent Publications EPO 0 214 731, and 0 284 176.

Avermectins are products of microbial fermentations using the actinomycete *Streptomyces avermitilis*. These microbes use acetates and propionates as building blocks for most of the avermectin carbon chain, which is then further modified by microbial enzymes to give the completed avermectin molecules. It is known, however, that the carbon C-25 and the 2-propyl and 2-butyl substituents at this carbon are not derived from acetate or propionate units, but are derived from aminoacids L-valine and L-isoleucine, respectively. It is believed that these aminoacids are deaminated to the corresponding 2-ketoacids, and that these then are decarboxylated to give 2-methylpropionic and 2-methylbutyric acids. These acids are then directly incorporated into the avermectin structures to give the 2-propyl and 2-butyl C-25 substituents, as is reported by Chen et al., Abstr. Pap. Am. Chem. Soc. (186 Meet., MBTD 28, 1983). It was also disclosed in European Patent Publication numbers 0 214 731 and 0 284 176 that additions of large amounts of other acids such as cyclopentanoic, cyclobutyric, 2-methylpentanoic, 2-methylhexanoic, thiophene-3-carboxylic acids and others to the fermentation broth of *S. avermitilis* causes the microbes to accept these acids as substitutes and to make small amounts of avermectins containing these acids in form of new C-25 substituents. Examples of such new avermectin derivatives are:

25-(thien-3-yl)-25-de-(2-butyl)avermectin A2a
25-(cyclohex-3-enyl)-25-de-(2-butyl)avermectin A2a
25-cyclohexyl-25-de-(2-butyl)avermectin A2a
25-(1-methylthioethyl)-25-de-(2-butyl)avermectin A2a
25-(2-methylcyclopropyl)-25-de-(2-butyl)avermectin A2a
25-(2-buten-2-yl)-25-de-(2-butyl) avermectin B1a
25-(cyclopentyl)-25-de-(2-butyl)-avermectin B1a Still additional avermectin derivatives are produced through artifical modification of the fermentation of *Streptomyces avermitilis* either by addition of metabolic inhibitors such as sinefungin (as described by Schulman et al., J. Antibiot. 1985 38, 1494–1498) or by mutation of the parent strain (as described by Schulman et al., Antimicrobial Agents and Chemotherapy, 1987, 31, 744–747, and by EP-276-131-A to Pfizer INC.). Some of these avermectin derivatives are still further modified and are missing one or two of the 3'- and 3"-O-methyl groups (Schulman et al., J. Antibiot. 1985, 38, 1494–1498). Examples for such derivatives are:

3',3''-O-Bisdesmethyl-25-cyclohexyl25-de-(2-butyl)-avermectin B1a

3',3''-O-Bisdesmethyl-25-cyclopentyl-25-de-(2-butyl)-avermectin B1a

3',3''-O-Bisdesmethyl-25-(3-thienyl)-25-de-(2-butyl)-avermectin B1a

3',3''-O-Bisdesmethyl-25-(3-furyl)-25-de-(2-butyl)-avermectin B1a

3',3''-O-Bisdesmethyl-25-(1-methylthioethyl)-25-de-(2-butyl)-avermectin B1a.

3''-O-Desmethylavermectin B1a/B1b

3'-O-Desmethylavermectin B1a/B1b

The fermentation products have been chemically modified in order to obtain further antiparasitic and insecticidal analogs with improved properties. Publications of such procedures in the scientific and patent literature have been reviewed by Fisher, M. H.; Mrozik, H. In Macrolide Antibiotics; Omura, S., Ed.; Academic: New York, 1984; pp 553–606, and by Davies, H. G.; Green, R. H. Nat. Prod. Rep., 1986, 3, 87–121.

For example, a group of semisynthetic avermectin derivatives were obtained by hydrogenating specifically the 22,23-double bond of avermectin B1 giving 22,23-dihydroavermectin B1 derivatives which have very potent anthelmintic and antiparasitic properties. Other examples of semisynthetic avermectin derivatives contain a 8,9-oxide group, a 4a-hydroxy or acyloxy group, a 23-keto group, which all are potent antiparasitic and insecticidal compounds.

These compounds may be used as starting materials for the compounds of the instant invention without further modification, or when containing additional reactive groups, which are not to be modified under the reaction conditions applied, only after protection of such with a suitable protecting group.

SUMMARY OF THE INVENTION

The instant invention is concerned with derivatives of avermectin compounds wherein the outer oleandrose ring of an avermectin or an avermectin monosaccharide compound is modified by addition of diazomethane to the 4''- or 4'-oxo-avermectin (I). The resultant compounds are homologated by one or more methylene groups and are spiro-epoxides (II) and perhydrooxepines (III, IV: the subject of a separate disclosure)(SCHEME 1). The spiro-eposides can be further modified. Thus it is the object of this invention to describe such compounds. It is a further object of this invention to describe the processes useful for the preparation of such compounds. A still further object is to describe the use of such compounds as anthelmintic, insecticidal, and acaricidal agents. Still further objects will become apparent from the reading of the following description.

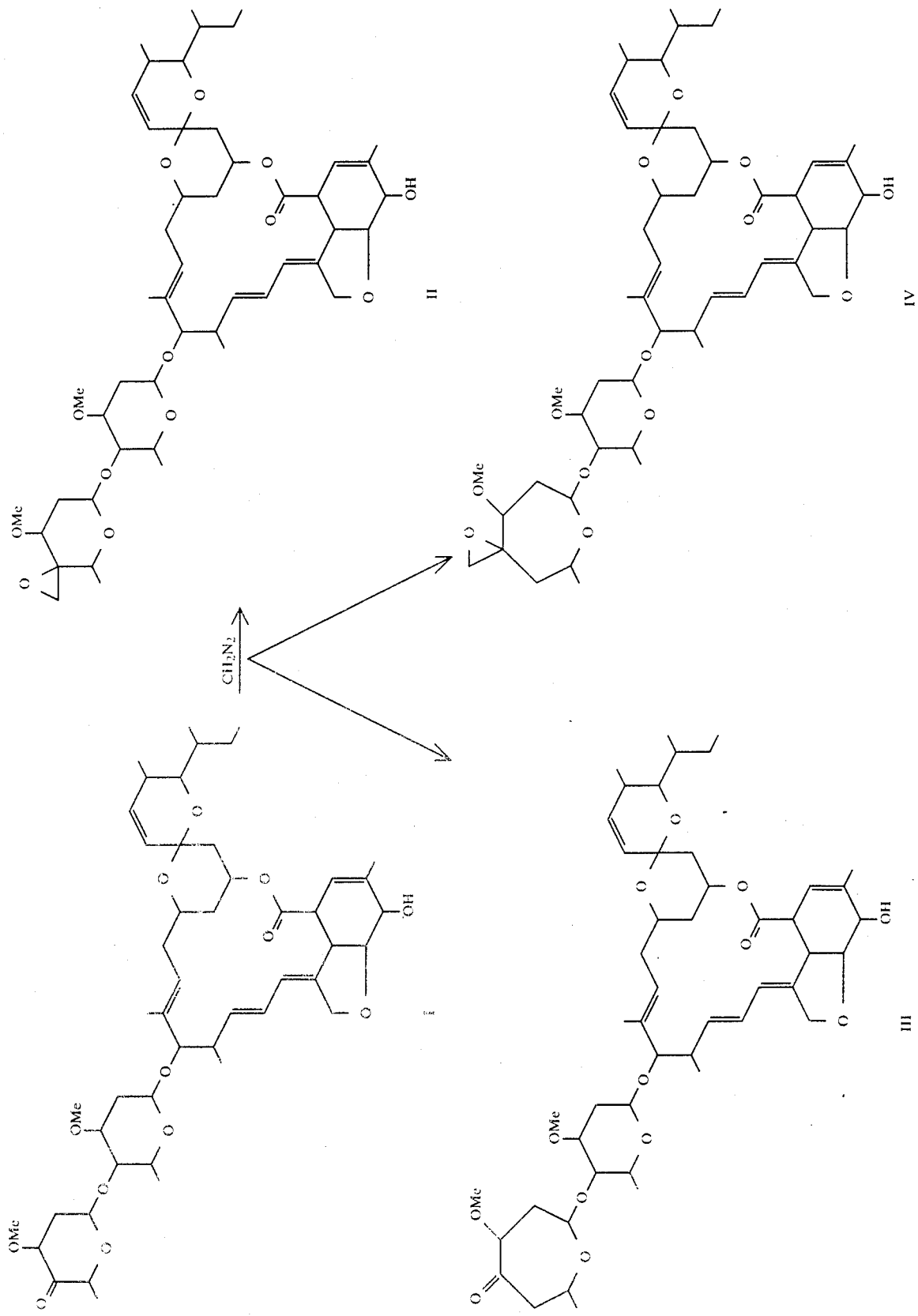

DESCRIPTION OF THE INVENTION

The compounds of the instant invention have the following structural formula:

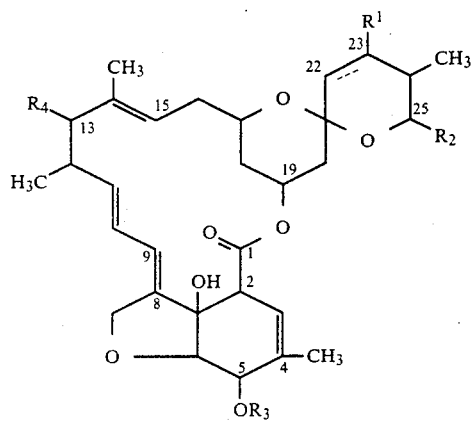

wherein the broken line at the 22,23 position represents a single bond and wherein $R_1$ is hydrogen or hydroxy or oxo, or the broken line represents a double bond and $R_1$ is absent;

$R_2$ is methyl, ethyl, or an alpha-branched $C_3$-$C_8$ alkyl or alkenyl group;

$R_3$ is hydrogen, loweralkyl or loweralkanoyl;

$R_4$ is

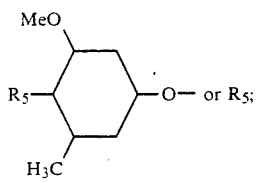

$R_5$ is

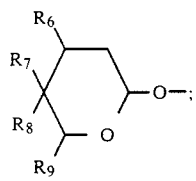

$R_6$ is hydrogen or loweralkoxy;

$R_7$ is halomethyl, phenylthiomethyl, hydroxymethyl, loweralkoxymethyl, loweralkanoyloxymethyl, aminomethyl, N-loweralkylaminomethyl, N,N-diloweralkylaminomethyl or loweralkanoylaminomethyl; and $R_8$ is hydroxy, loweralkanoyloxy; or $R_7$ and $R_8$ together are methylene, or —$CH_2O$—;

$R_9$ is loweralkyl.

Preferred compounds of the instant invention are realized in the foregoing structural formula wherein the broken line at the 22,23 position represents a single bond and wherein $R_1$ is hydrogen or hydroxy or oxo, or the broken line represents a double bond and $R_1$ is absent;

$R_2$ is iso-propyl, sec-butyl, or an alpha-branched $C_3$-$C_8$ alkenyl group;

$R_3$ is hydrogen;

$R_4$ is

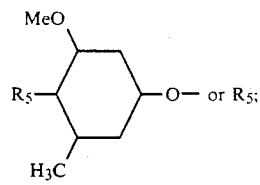

$R_5$ is

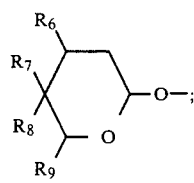

$R_6$ is hydrogen or methoxy:

$R_7$ is iodomethyl, phenylthiomethyl, hydroxymethyl, loweralkoxymethyl, loweralkanoyloxymethyl, aminomethyl, N-loweralkylaminomethyl, N,N-diloweralkylaminomethyl or loweralkanoylaminomethyl; and $R_8$ is hydroxy; or $R_7$ and $R_8$ together are methylene, or —$CH_2O$—;

$R_9$ is methyl.

The most preferred compounds of the instant invention are realized in the foregoing structural formula wherein the broken line at the 22,23 position represents a single bond and wherein $R_1$ is hydrogen or hydroxy or oxo, or the broken line represents a double bond and $R_1$ is absent;

$R_2$ is iso-propyl, sec-butyl, or an alpha-branched $C_3$-$C_6$ alkenyl group;

$R_3$ is hydrogen;

$R_4$ is

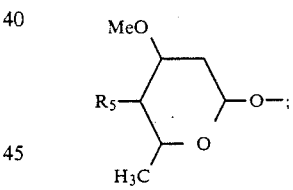

$R_5$ is

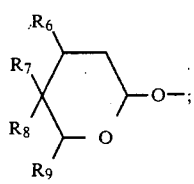

$R_6$ is hydrogen or methoxy;

$R_7$ is iodomethyl, phenylthiomethyl, hydroxymethyl, loweralkoxymethyl, loweralkanoyloxymethyl, aminomethyl, N-loweralkylaminomethyl, N,N-diloweralkylaminomethyl or loweralkanoylaminomethyl; and $R_8$ is hydroxy; or $R_7$ and $R_8$ together are methylene, or —$CH_2O$—;

$R_9$ is methyl.

Preferred compounds of the instant invention are further realized in the following compounds:

4''-exomethylene-avermectin B1a/B1b-4''', 4''a-oxide isomer a

4''-exomethylene-avermectin B1a/B1b-4''', 4''a-oxide isomer b

4''-deoxy-4''-exomethylene-avermectin B1a/B1b

4''-iodomethyl-avermectin B1a/B1b

4''-phenylthiomethyl-avermectin B1a/B1b

4''-exomethylene-avermectin B2a/B2b-4″, 4″a-oxide
4″-deoxy-4″-exomethylene-avermectin B2a/B2b
4″-iodomethyl-avermectin B2a/B2b
25-cylopentyl-25-de-(1-methylpropyl)-4″-exomethylene-avermectin B1a-4″, 4″a-oxide
22,23-dihydro-4″-exomethylene-avermectin B1a/B1b-4″, 4″a-oxide In the instant invention the term "loweralkyl" is intended to indicate those alkyl groups of from 1 to 6 carbon atoms in either a straight or branched chain such as methyl, ethyl, propyl, isopropyl, butyl, pentyl, hexyl, and the like.

The term "loweralkoxy" is intended to include those alkoxy groups in either a straight or branched chain of from 1 to 6 carbon atoms such as methoxy, ethoxy, propoxy, isopropoxy, butoxy, pentoxy, hexoxy, and the like.

The term "loweralkanoyl" is intented to include those alkanoyl groups in either a straight or branched chain of from 1 to 6 carbon atoms such as formyl, acetyl, propionyl, butyryl, pentanoyl, hexanoyl, and the like.

The term "halogen" is intended to include the halogen atoms, fluorine, chlorine, bromine, or iodine.

The above structural formula is shown without a definitive sterochemistry. However, during the course of the synthetic procedures used to prepare such compounds, the products of such procedures can be a mixture of stereoisomers. In particular, the stereoisomers at the 13- and 23-positions may be oriented either $\alpha$- or $\beta$-representing such groups being below or above the general plane of the molecule, respectively. In each such case both the $\alpha$- and $\beta$- configurations are intended to be included within the ambit of this invention.

PREPARATION OF STARTING MATERIALS

The ultimate starting materials for the compounds of this invention are the avermectin fermentation products defined above. In addition, other microbially produced avermectin derivatives containing an alpha branched alkyl or alkenyl group substituent at the 25 position designated in the structural formula as $R_2$ have been described in European patent application number 86305604.0 (publication number 0 214 731), 88300426.9 (0 276 131), and 88300354.3 (0 276 103). These compounds can also be used as starting materials for the compounds claimed in this invention. The $R_2$ substituent is inert under the reaction conditions employed for the preparation of the compounds of this invention, so that these reactions can also be carried out with these altered avermectin derivatives. It is apparent that additional reactions are required to prepare the instant compounds. Specifically, reactions are carried out at the 5, 22, and 23-positions. It is generally preferred to prepare whatever substituents are required at these positions before the oxidation at the 4″-hydroxy and subsequent substitution on the thus produced 4″-ketone. Such a procedure generally avoids undesirable side reactions. This technique is not required, however, and if desired other sequences may be used. In addition, during the oxidation and substitution reaction described above, it is necessary to protect the hydroxy group at the 5-position to avoid oxidation or substitution at such position. With this position protected the reactions may be carried out at the 4″-or 4′-positions without affecting the remainder of the molecule. Subsequent to any of the above described reactions the protecting group may be removed and the unprotected product isolated. The protecting group employed is ideally one which may be readily synthesized, will not be affected by the reactions at the 4″-and 4′-positions and may be removed without affecting any other functionality of the molecule. One preferred type of protecting group for the avermectin type of molecule is the tri-substituted silyl group, preferably the trialkyl silyl group. One especially preferred example is the t-butyldimethylsilyl group. The reaction preparing the protected compound is carried out by reacting the hydroxy compound with the appropriately substituted silylhalide, preferably the silylchloride in an aprotic polar solvent such as methylene chloride, benzene, toluene, ethyl acetate, tetrahydrofuran, dimethylformamide and the like. In order to minimize side reactions, there is included in the reaction mixture a base to react with the acid halide released during the course of the reaction. Preferred amines are imidazole, pyridine, or triethylamine. The base is required in amounts equimolar to the amount of hydrogen halide liberated; however, generally several equivalents of the amine are employed. The reaction is stirred at from 0° C. to the reflux temperature of the reaction mixture and is complete in from ½ to 16 hours.

The silyl group is removed by stirring the silyl compound in methanol catalized by an acid preferably a sulfonic acid monohydrate such as p-toluenesulfonic acid monohydrate. The reaction is complete in about 0.5 to 12 hours at from 0° to 50° C. Alternatively, the silyl group may be removed by treatment of the silyl compound with anhydrous pyridine-hydrogen fluoride in tetrahydrofuran. The reaction is complete in from 3 to 24 hours at from 0° to 25° C.

Another of the starting materials used in the foregoing reaction scheme are those in which the 22,23, double bond has been reduced to a single bond. The preferred catalyst for the selective hydrogenation of the 22,23 bond is one having the formula:

$$[((R_{10})_3P)_3RhY]$$

wherein $R_{10}$ is loweralkyl, phenyl, or loweralkyl substituted phenyl and Y is halogen. The reduction is completely described in U.S. Pat. No. 4,199,569.

The other starting materials which are used in the above reaction scheme involve the preparation of the monosaccharide. The processes which may be used to prepare the monosaccharide derivatives of the avermectin compounds are described in U.S. Pat. No. 4,206,205. The reaction consists generally of treating the starting disaccharide with acid in an aqueous organic solvent mixture. Water concentration of from 0.1 to 20% by volume and acid concentrations of from about 0.01 to 0.1% will predominantly produce the monosaccharide.

A further procedure for the preparation of the monosaccharide utilizes a 1% mineral acid solution in is propanol at 20° to 40° C. for from 6 to 24 hours. Mineral acids such as sulfuric, phosphoric, and the like may be employed.

In all cases the substituent at the 25-position of the avermectin is inert to the reaction conditions and the presence of alkyl groups, alkenyl groups, cycloalkyl groups, cycloalkenyl groups and the like at this position will little affect the preparation, isolation, or activity of the avermectin derivative.

PREPARATION OF COMPOUNDS

The preparation of the instant compounds requires that the avermectin starting materials are oxidized at the 4'-or 4"-position to the corresponding oxo compounds. During the procedure the presence of a hydroxy group at the 5-position will require that such group be protected in order that it too is not oxidized. The 23-hydroxy group is less reactive and the 7-hydroxy group is very unreactive and they need not be protected. The procedure used to prepare the protected intermediates are described above. The oxidation reaction is carried out in an inert solvent such as methylene chloride using oxalyl chloride or trifluoroacetic anhydride and dimethylsulfoxide as the oxidizing agent. Additionaly, N-chlorosuccinimide and dimethylsulfide may be employed. The reaction proceeds by dissolving the oxalyl chloride or trifluoroacetic anhydride and dimethylsulfoxide (or other oxidizing agent) in methylene chloride with cooling from $-50°$ to $-80°$ C. and adding dropwise a methylene chloride solution of the avermectin compound to be oxidized. The addition is carried out over a period of from 15 minutes to 1 hour and then triethylamine is added dropwise over a period of from 1 to 15 minutes. The reaction mixture is then allowed to warm to room temperature over a period of from $\frac{1}{2}$ to 1 hour. The 4"-or 4'-oxo compound is isolated using techniques known to those skilled in the art.

Homologation of avermectin is carried out by treatment of 4"-oxo-avermectin with an ether solution of diazomethane in an organic solvent such as ether, tetrahydrofuran, methanol, ethanol, methylene chloride and the like. Simple evaporation and isolation by techniques known to those skilled in the art afford the methylene-homologated derivatives including 4"-exomethylene-avermectin B1a/B1b-4", 4"a-oxide isomer a, 4"-exomethylene-avermectin B1a/B1b-4", 4"a-oxide isomer b, 4'-O-[2-(4-methoxy-7-methyloxepin-5-onyl)]-avermectin B1a/B1b monosaccharide, 4'-O-[2-(5-exomethylene- 4-methoxy-7-methyl-5, 5a-oxo-oxepinyl)]-avermectin B1a/B1b monosaccharide (SCHEME 1).

4"-deoxy 4"-exomethylene-avermectin and 4"-iodomethyl-avermectin can be prepared by the treatment of 4"-exomethylene-avermectin B1-4", 4"a-oxide with $SmI_2$ or $YbI_2$ in an organic solvent such as ether, tetrahydrofuran and the like at -78° to 25° C. for 2 to 12 hours. The products are isolated and purified by techniques known to those skilled in the art.

Treatment of 4"-exomethylene-avermectin B1a/B1b-4", 4"a-oxide with a nucleophile such as an alcohol, amine, mercaptan or the like in an organic solvent such as tetrahydrofuran, dimethylformamide, pyridine and the like with or without added base such as pyridine, triethylamine, and the like, and with or without added catalyst such as dimethylaminopyridine, potassium tert-butoxide and the like gives the corresponding 4"a-substituted avermectin derivatives. Alternatively, 4"-iodomethyl-avermectin can be used in place of 4"-exomethylene-avermectin B1a/B1b-4", 4"a-oxide. The products are isolated and purfied by techniques known to those skilled in the art.

The novel compounds of this invention have significant parasiticidal activity as anthelmintics, ectoparasiticides, insecticides, and acaracides, in human and animal health and in agriculture.

The disease or group of diseases described generally as helminthiasis is due to infection of an animal host with parasitic worms known as helminths. Helminthiasis is a prevalent and serious economic problem in domesticated animals such as swine, sheep, horses, cattle, goats, dogs, cats, and poultry. Among the helminths the group of worms described as nematodes causes widespread and oftentimes serious infection in various species of animals. The most common genera of nematodes infecting the animals referred to above are Haemonchus, Trichostronglylus, Ostertagia, Nematodirus, Cooperia, Ascaris, Bunostomum, Oesophagostomum, Chabertia, Trichuris, Strongylus, Trichonema, Dictocaulus, Capillaria, Heterakis, Toxocara, Ascaridia, Oxyuris, Ancylostoma, Uncinaria, Toxascaris, and Parascaris. Certain of these, such as Nematodirus, Cooperia, and Oesophagostomum attack primarily the intestinal tract while others, such as Haemonchus and Ostertagia, are more prevalent in the stomach while still others such as Dictocaulus are found in the lungs. Still other parasites may be located in other tisues and organs of the body such as the heart and blood vessels, subcutaneous and lymphatic tissue and the like. The parasitic infections known as helminthiasis lead to anemia, malnutrition, weakness, weight loss, severe damage to the walls of the intestinal tract and other tissues and organs and, if left untreated, may result in the death of the infected host. The hydrogenated avermectin compounds of this invention have unexpectedly high activity against Dirofilaria in dogs, Nematospiroides, Syphacia, Aspiculuris in rodents, anthropod ectoparasties of animals and birds such as ticks, mites, lice, fleas, blowfly, in sheep Lucilia sp., biting insects and such migrating dipterous larvea as Hypoderma sp. in cattle, Gastrophilus in horses, and Cuterebra sp. in rodents.

The instant compounds are also useful against parasites which infect humans. The most common genera of parasites of the gastro-intestinal tract of man are Ancylostoma, Necator, Ascaris, Strongyloides, Trichinella, Capillaria, Trichuris, and Enterobius. Other medically important genera of parasites which are found in the blood or other tissues and organs outside the gastrointestinal tract are the filiarial worms such as Wuchereria, Brugia, Onchocerca and Loa, Dracunculus and extra-intestinal stages of the intestinal worms Strongyloides and Trichinella. The compounds are also of value against arthropods parasitizing man, biting insects and other dipterous pests causing annoyance to man.

The compounds are also active against household pests such as the cockroach, Blatella sp., clothes moth, Tineola sp., carpet beetle, Attagenus sp., and the housefly *Musca domestica.*

The compounds are also useful against insect pests of stored grains such as Tribolium sp., Tenebrio sp. and of agricultural plants such as spider mites (Tetranychus sp.) aphids (Acyrthiosiphon sp.); against migratory orthopterans such as locusts and immature stages of insects living on plant tissue. The compounds are useful as a nematocide for the control of soil nematodes and plant parasites such as Meloidogyne spp. which may be of importance in agriculture.

These compounds may be administered orally in a unit dosage form such as a capsule, bolus or tablet, or as a liquid drench where used as an anthelmintic in mammals. The drench is normally a solution, suspension or dispersion of the active ingredient usually in water together with a suspending agent such as bentonite and a wetting agent or like excipient. Gradually, the drenches also contain an antifoaming agent. Drench formulations generally contain from about 0.001 to 5% by weight of the active compound. Preferred drench formulations may contain from 0.01 to 0.1% by weight active compound. The capsules or boluses are comprised of the active ingredient admixed with a carrier vehicle such as starch, talc, magnesium stearate, or di-calcium phosphate.

Where it is desired to administer the avermectin derivatives in a dry, solid unit dosage form, capsules, boluses, or tablets containing the desired amount of active compound usually are employed. The dosage forms are prepared by intimately and uniformly mixing the active ingredients with suitable finely divided diluents, fillers, disintegrating agents, and/or binders such as starch, lactose, talc, magnesium stearate, vegetable gums and the like. Such unit dosage formulations may be varied widely with respect to their total weight and content of antiparasitic agent depending upon factors such as the type of host animal to be treated, the severity and type of the infection and the weight of the host.

When the active compound is to be administered via the animal feedstuff, it is intimately dispersed in the feed or used as a top dressing or in the form of pellets which may then be added to the finished feed or optionally fed separately. Alternatively, the antiparasitic compounds of our invention may be administered to the animals parenterally, for example, by intraruminal, intramuscular, intratracheal, or subcutaneous injection in which the active ingredient is dissolved or dispersed in a liquid carrier vehicle. For parenteral administration, the active material is suitably admixed with an acceptable vehicle, preferably of the vegetable oil variety such as peanut oil, cotton seed oil, and the like. Other pareteral vehicles such as organic preparation using solketal, glycerol formal, and aqueous parental formulations are also used. The active monosaccharide or aglycone avermectin compound or compounds are dissolve or suspended in the parenteral formulation for administration; such formulations generally contain from 0.005 to 5% by weight of the active compound.

Although the antiparasitic agents of this invention find their primary use in the treatment and/or prevention of helminthiasis, they are also useful in the prevention and treatment of diseases caused by other parasites, for example, arthropod parasites such as ticks, lice, fleas, mites, and other biting insects in domesticated animals and poultry. They are also effective in treatment of parasitic diseases that occur in other animals including humans. The optimum amount to be employed for the best results will, of course, depend upon the particular compound employed, the species of animal to be treated and the type and severity of parasitic infection or infestation. Generally good results are obtained with our novel compounds by the oral administration of from about 0.001 to 10 mg per kg of animal body weight, such total dose being given at one time or in divided doses over a relatively short period of time such as 1-5 days. With the preferred compounds of the invention, excellent control of such parasites is obtained in animals by administering from about 0.025 to 0.5 mg per kg of body weight in a single dose. Repeat treatments are given as required to combat re-infections and are dependent upon the species of parasite and the husbandry techniques being employed. The techniques for administering these materials to animals are known to those skilled in the veterinary field. When the compounds described herein are administered as a component of the feed of the animals, or dissolved or suspended in the drinking water, compositions are provided in which the active compound or compounds are intimately dispersed in an inert carrier or diluent. By inert carrier is meant one that will not react with the antiparasitic agent and one that may be administered safely to animals. Preferably, a carrier for feed administration is one that is, or may be, an ingredient of the animal ration.

Suitable compositions include feed premixes or supplements in which the active ingredient is present in relatively large amounts and which are suitable for the direct feeding to the animal or for addition to the feed either directly or after an intermediate dilution or blending step. Typical carriers or diluents suitable for such compositions include, for example, distillers' dried grains, corn meal, citrus meal, fermentation residues, ground oyster shells, wheat shorts, molasses solubles, corn cob meal, edible bean mill feed, soya grits, crushed limestone and the like. The active avermectin compounds are intimately dispersed throughout the carrier by methods such as grinding, stirring, milling, or tumbling. Compositions containing from about 0.005 to 2.0% weight of the active compound are particularly suitable as feed premixes. Feed supplements, which are fed directly to the animal, contain from about 0.002 to 0.3% by weight of the active compounds.

Such supplements are added to the animal feed in an amount to give the finished feed the concentration of active compound desired for the treatment and control of parasitic diseases. Although the desired concentration of the active compound will vary depending upon the factors previously mentioned as well as upon the particular avermectin derivative employed, the compounds of this invention are usually fed at concentrations of between 0.00001 to 0.002% in the feed in order to achieve the desired antiparasitic result.

In using the compounds of this invention, the individual avermectin components may be prepared and used in that form. Alternatively, mixtures of two or more of the individual avermectin components may be used, or other active compounds not related to the compounds of this invention.

The compounds of this invention are also useful in combatting agricultural pests that inflict damage upon crops while they are growing or in storage. The compounds are applied using known techniques as sprays, dusts, emulsions and the like, to the growing or stored crops to effect protection from such agricultural pests.

The following examples are provided in order that this invention might be more fully understood; they are not to be construed as limitative of the invention.

The avermectin derivatives prepared in the following examples are generally isolated as amorphous solids and not as crystalline solids. They are thus characterized analytically using techniques such as mass spectrometry, nuclear magnetic resonance spectrometry and the like. Being amorphous, the compounds are not characterized by sharp melting points, however, the chromatographic and analytical methods employed indicate that the compounds are pure.

EXAMPLE 1

4''-Exomethylene-avermectin B1a/B1b-4''', 4''a-oxide isomer a and
4'-O-[2-(4-methoxy-7-methyloxepin-5-onyl)]-avermectin B1a/B1b monosaccharide To a stirred solution of 4''-oxo-avermectin B1a/B1b (100 mg., 0.115 mmol., 1 eq.) in ether (2 mL.) in a 16 mL. screw-cap vial was added a solution of diazomethane in ether (3.5 mL., 1.15 mmol., 10 eq., 0.33M). The vial was capped and the mixture stirred. After 24 h the mixture was concentrated in vacuo. The products were isolated by preparative TLC on silica gel (eluted with 3:1 hexanes/acetone) to afford 35.1 mg. 4''-exomethylene-avermectin B1a/B1b-4''', 4''a-oxide isomer a and 13.7 mg. 4'-O-[2-(4-methoxy-7-methyloxepin-5-onyl)]-avermectin B1a/B1b monosaccharide characterized by $^1$H NMR and mass spectral analysis.

EXAMPLE 2

4''-Exomethylene-avermectin B1a/B1b-4''', 4''a-oxide isomer a, 4''-exomethylene-avermectin B1a/B1b-4''',4''a-oxide isomer b and
4'-O-[2-(5-exomethylene-4-methoxy-7-methyl-5,5a-oxo-oxepinyl)]-avermectin B1a/B1b monosaccharide To a stirred solution of 4''-oxo-avermectin B1a/B1b (100 mg., 0.115 mmol., 1 eq.) in methanol (2 mL.) in a 16 mL. screw-cap vial was added a solution of diazomethane in ether (3.5 mL., 1.15 mmol., 10 eq., 0.33M). The vial was capped and the mixture stirred. After 24 h the mixture was concentrated in vacuo. The products were isolated by preparative TLC on silica gel (eluted with 3:1 hexanes/acetone) to afford 43.1 mg. 4''-exomethylene-avermectin B1a/B1b-4''', 4''a-oxide isomer a, 7.2 mg. and 13.7 mg. 4''-exomethylene-avermectin B1a/B1b-4''', 4,''a-oxide isomer b, and 13.3 mg 4'-O-[2-(5-exomethylene-4-methoxy-7-methyl-5,5a-oxo-oxepinyl)]-avermectin B1a/B1b monosaccharide characterized by $^1$H NMR and mass spectral analysis.

EXAMPLE 3

4''-deoxy-4''-Exomethylene-avermectin B1a/B1b and
4''-iodomethyl-avermectin B1a/B1b To a 16 mL. screw-cap vial equipped with a septum cap and a magnetic stir bar was added a solution of SmI$_2$ in tetrahydrofuran (4.5 mL., 0.179 mmol., 5 eq., 0.04M). The vial was placed under N$_2$ and cooled to $-78°$ C. To the SmI$_2$ solution was added a solution of 4''-exomethylene-avermectin B1a/B1b-4''', 4''a-oxide (31.8 mg., 0.036 mmol., 1 eq.) and tert-butanol (0.030 mL., 0.108 mmol., 3 eq.) in tetrahydrofuran (0.5 mL.). After the addition was complete the dark blue solution was allowed to warm to room temperature. The reaction mixture was stirred for 16 h at room temperature under N$_2$. During the reaction the color of the mixture changed from blue to yellow and a precipitate formed. The reaction was quenched with saturated aqueous NaHCO$_3$, diluted with water and extracted 5× with methylene chloride. The organic extracts were combined, dried over anhydrous sodium sulfate, filtered and concentrated in vacuo. The products were isolated by preparative TLC on silica gel (eluted with 3:1 hexanes-/acetone) affording 14.0 mg 4''-deoxy-4''-exomethylene-avermectin B1a/B1b, and 12.9 mg 4''-iodomethyl-avermectin B1a/B1b characterized by $^1$H NMR and mass spectral analysis.

EXAMPLE 4

4''-Phenylthiomethyl-avermectin B1a/B1b

To a stirred solution of 4''-exomethylene-avermectin B1a/B1b-4''', 4''a-oxide isomer a (15.7 mg., 0.018 mmol., 1 eq.) in pyridine (1 mL.) was added thiophenol (0.10 mL., 0.974 mmol., 54 eq.). The mixture was stirred at room temperature. After 3.5 h a flake of potassium tert-butoxide was added to catalyse the reaction. The mixture was stirred for 16 h. The mixture was concentrated in vacuo and the products isolated by preparative TLC on silica gel (eluted with 3:1 hexanes/acetone) to afford 8.0 mg. 4''-phenylthiomethyl-avermectin B1a/B1b characterized by $^1$H NMR and mass spectral analysis.

EXAMPLE 5

5-0-tert-Butyldimethylsilyl-avermectin B2a/B2b

To a stirred solution of avermectin B2a/B2b (100 mg.) in dry dimethylformamide (1 mL.) is added tert-butyldimethylsilylchloride (48 mg.) and imidazole (48 mg.) and the mixture is stirred at room temperature for 50 minutes. The reaction mixture is then diluted with water and extracted 3× with methylene chloride. The organic extracts are combined, dried over anhydrous sodium sulfate, filtered and concentrated in vacuo. The product mixture is separated by silica gel column chromatography with a methylene chloride/ethylacetate 90:10 to 70:30 solvent system to give 5-0-tert-Butyldimethylsilyl-avermectin B2a/B2b characterized by $^1$H NMR and mass spectral analysis.

EXAMPLE 6

4''-Oxo-5-O-tert-butyldimethylsilyl-avermectin B2a/B2b

To a dried flask purged with N$_2$ is added oxalyl chloride (0.097 mL.) and methylene chloride (1.5 mL.). The reacton mixture is cooled to $-78°$ C. and a solution of dimethylsulfoxide (0.169 mL.) in methylene chloride (1 mL.) is added over 3 min and the reaction mixture is stirred for two minutes at $-78°$ C. To the reaction mixture is added a solution of 5-O-tert-Butyldimethylsilyl-avermectin B2a/B2b (500 -mg.) in methylene chloride (3 mL.) dropwise over 5 minutes and the mixture is stirred at $-78°$ C. for 30 minutes. At the end of this period triethylamine (0.71 mL.) is added dropwise and the reaction mixture is allowed is stirred at $-78°$ C. for 5 minutes. The cooling bath is removed and the reaction is allowed to come to room temperature over a period of 45 minutes. The reaction is quenched by addition of 50 mL. of water and is extracted 4× with methylene chloride. The organic extracts are combined, dried over anhydrous sodium sulfate, filtered, and concentrated in vacuo. The product mixture is separated by preparative TLC on silica gel to afford 4''-oxo-5-0-tert-butyldimethylsilyl-avermectin B2a/B2b, 23-oxo-5-0-tert-butyldimethylsilyl-avermectin B2a/B2b, and 4'', 23-bis-oxo-5-0tert--butyldimethylsilyl-avermectin B2a/B2b characterized by $^1$H NMR and mass spectral analysis.

EXAMPLE 7

4''-oxo-avermectin B2a/B2b

4''-oxo-5-0-tert-butyldimethyl-avermectin B2a/B2b (100 mg) is treated with a solution of HF. pyridine and pyridine in tetrahydrofuran (1 mL. of a solution of 15 mL. HF. pyridine plus 60 mL. pyridine plus 120 mL. tetrahydrofuran) for 6 h. The reaction mixture is quenched with saturated aqueous sodium bicarbonate and extracted 5× with methylene chloride. The organic extracts are combined, dried over anhydrous sodium sulfate, filtered and concentrated in vacuo. The product is isolated by preparative TLC chromatography on silica gel to afford 4"-oxo-avermectin B2a/B2b characterized by $^1$H NMR and mass spectral analysis.

EXAMPLE 8

4"-Exomethylene-avermectin B$_2$-4",4"a-oxide and 4'-O-[2-(4-methoxy-7-methyloxepin-5-onyl)]-avermectin B$_2$ monosaccharide To a stirred solution of 4"-oxo-avermectin B2a/B2b (100 mg.) in ether (2 mL.) in a 16 mL. screw-cap vial is added a solution of diazomethane in ether (3.5 mL., 0.33M). The vial is capped and the mixture stirred. After 24 h the mixture is concentrated in vacuo. The products are isolated by preparative TLC on silica gel giving 4"-exomethylene-avermectin B2a/B2b-4",4"a-oxide and 4'-O-[2-(4-methoxy-7-methyloxepin-5-onyl)]-avermectin B2a/B2b monosaccharide characterized by $^1$H NMR and mass spectral analysis.

EXAMPLE 9

4"-deoxy-4"-Exomethylene-avermectin B2a/B2b and 4"-iodomethyl-avermectin B2a/B2b A solution of 4"-exomethylene-avermectin B2a/B2b-4",4"a-oxide (31.8 mg.) and tert-butanol (0.03 mL.) in tetrahydrofuran (0.5 mL.) is added to a solution of SmI$_2$ in tetrahydrofuran (4.5 mL., 0.04M) in accordance with the procedure completely described in Example 3 giving 4"-deoxy 4"-exomethylene-avermectin B2a/B2b and 4"-iodomethyl-avermectin B2a/B2b characterized by $^1$H NMR and mass spectral analysis.

EXAMPLE 10

25-Cylopentyl-25-de-(1-methylpropyl)-5-O-tert-butyldim ethylsilyl-avermectin B1a A solution of 25-cylopentyl-25-de-(1-methylpropyl)-avermectin B1a (100 mg.), imidazole (48 mg.), tert-butyldimethylsilylchloride (48 mg.) in dry dimethylformamide (1.0 mL.) is treated in accordance with the procedure fully described in Example 5 to afford 25-cylopentyl-25-de-(1-methylpropyl)-5-O-tert-butyldimethylsilyl-avermectin B1a characterized by $^1$H NMR and mass spectral analysis.

EXAMPLE 11

25-Cylopentyl-25-de-(1-methylpropyl)-5-O-tert-butyldim ethylsilyl-4"-oxo-avermectin B1a To a dried flask purged with nitrogen is added oxalyl chloride (0.097 mL.) and methylene chloride (1.5 mL.). The reaction mixture is cooled to −78° C. and a solution of dimethylsulfoxide (0.169 mL.) in methylene chloride (1 mL.) is added over 3 min and the reaction mixture is stirred for two minutes at −78° C. To the reaction mixture is added a solution of 25-cylopentyl-25-de-(1-methylpropyl)-5-O-tert-butyldimethylsilyl-avermectin B1a (500 mg.) in methylene chloride (3 mL.) dropwise over 5 minutes and the mixture is stirred at −78° C. for 30 minutes. At the end of this period triethylamine (0.71 mL.) is added dropwise and the reaction mixture is stirred at −78° C. for 5 minutes. The cooling bath is removed and the reaction is allowed to come to room temperature over a period of 45 minutes. The reaction is quenched by addition of 50 mL. of water and is extracted 4 times with methylene chloride. The organic extracts are combined, dried over anhydrous sodium sulfate, filtered, and concentrated in vacuo. The product mixture is separated by preparative TLC on silica gel to afford 25-cylopentyl-25-de-(1-methylpropyl)-5-O-tert-butyldimethylsilyl-4"-oxo-avermectin B1a characterised by $^1$H NMR and mass spectral analysis.

EXAMPLE 12

25-Cylopentyl-25-de-(1-methylpropyl)-4"-oxo-avermectin B1a

25-Cylopentyl-25-de-(1-methylpropyl)-5-O-tert-butyldimethylsilyl-4"-oxo-avermectin B1a (100 mg) is treated with a solution of HF.pyridine and pyridine in tetrahydrofuran (1 mL. of a solution of 15 mL. HF.pyridine plus 60 mL. pyridine plus 120 mL. tetrahydrofuran) in accordance with the procedure fully described in Example 7 to give 25-cylopentyl-25-de-(1-methylpropyl)-4"-oxo-avermectin B1a.

EXAMPLE 13

25-Cylopentyl-25-de-(1-methylpropyl)-4"-exomethylene-a vermectin B1-4",4"a-oxide and 25-cylopentyl-25-de-(1-methylpropyl)-4'-O-[2-(4-methoxy-7-methyloxepin-5-onyl)]-avermectin B1a monosaccharide A solution of 25-cylopentyl-25-de-(1-methylpropyl)-4"-oxo-avermectin B1a (100 mg) in ether (2 mL.) is reacted with an ether solution of diazomethane (3.5 mL., 0.33M) in accordance with the procedure fully described in Example 8 to give 25-cylopentyl-25-de-(1-methylpropyl)-4"-exomethylene-avermectin B1a-4",4"a-oxide and 25-cylopentyl-25-de-(1-methylpropyl)-4'-O-[2-(4-methoxy-7-methyloxepin-5-onyl)]-avermectin B1a monosaccharide characterized by $^1$H NMR and mass spectral analysis.

EXAMPLE 14

22,23-Dihydro-5-O-tert-Butyldimethylsilyl-avermectin B1a/B1b

A stirred solution of 22,23-dihydro-avermectin B1a/B1b (100 mg.) in dry dimethylformamide (1 mL) is treated with tert-butyldimethylsilyl-chloride (48 mg) in accordance with the procedure fully described in Example 5 to afford 22,23-dihydro-5-O-tert-Butyldimethylsilyl-avermectin B1a/B1b characterized by $^1$H NMR and mass spectral analysis.

EXAMPLE 15

22,23-Dihydro-4"-oxo-5-O-tert-Butyldimethylsilyl-averm ectin B1a/B1b

To a dried flask purged with nitrogen is added oxalyl chloride (0.097 mL.) and methylene chloride (1.5 mL.). The reacton mixture is cooled to −78° C. and a solution of dimethylsulfoxide (0.169 mL.) in methylene chloride (1 mL.) is added over 3 min and the reaction mixture is stirred for two minutes at −78° C. To the reaction mixture is added a solution of 22,23-dihydro-5-O-tert-Butyldimethylsilyl-avermectin B1(500 mg.) in methylene chloride (3 mL.) dropwise over 5 minutes and the mixture is stirred at −78° C. for 30 minutes. At the end of this period triethylamine (0.71 mL.) is added dropwise and the reaction mixture is allowed is stirred at −78° C. for 5 minutes. The cooling bath is removed and the reaction is allowed to come to room temperature over a period of 45 minutes. The reaction is quenched by addition of 50 mL. of water and is extracted 4x with methylene chloride. The organic extracts are combined, dried over anhydrous sodium sulfate, filtered, and concentrated in vacuo. The product mixture is separated by preparative TLC on silica gel to afford 22,23-dihydro-4″-oxo-5-O-tert-butyldimethylsilyl-avermectin B1a/B1b characterized by $^1$H NMR and mass spectral analysis.

EXAMPLE 16

22,23-Dihydro-4″-oxo-avermectin B1a/B1b 22,23-dihydro-4″-oxo-5-O-tert-butyldimethylsilyl-avermectin B1a/B1b (100 mg) is treated with a solution of HF.pyridine and pyridine in tetrahydrofuran (1 mL. of a solution of 15 mL. HF.pyridine plus 60 mL. pyridine plus 120 mL. tetrahydrofuran) in accordance with the procedure fully described in Example 7 to give 22,23-dihydro-4″-oxo-avermectin B1a/B1b characterized by $^1$H NMR and mass spectral analysis.

EXAMPLE 17

22,23-Dihydro-4″-exomethylene-avermectin B1a/B1b-4″,4″a-oxide and 22,23-dihydro-4′-O-[2-(4-methoxy-7-methyloxepin-5-onyl)]-avermectin B1a/B1b monosaccharide A solution of 22,23-dihydro-4″-oxo-avermectin B1a/B1b (100 mg) in ether (2 mL.) is reacted with an ether solution of diazomethane (3.5 mL., 0.33M) in accordance with the procedure fully described in Example 8 to give 22,23-dihydro-4″-exomethylene-avermectin B1a/B1b-4″a-oxide and 22,23-dihydro-4′-O-[2-(4-methoxy-7-methyloxepin-5-onyl)]-avermectin B1a/B1b monosaccharide characterized by $^1$H NMR and mass spectral analysis.

EXAMPLE 18

4″-N-Ethyl-aminomethyl-avermectin B1a/B1b

To a stirred solution of 4″-exomethylene-avermectin B1a/B1b-4″,4″a-oxide (50 mg.) in methanol (2 mL.) is added ethylamine (0.5 mL. 70% aqueous solution) and the mixture is stirred for 6 hours at room temperature. The reaction mixture is diluted with water and extracted 4× with methylene chloride. The organic extracts are combined, dried over anhydrous $Na_2CO_3$, filtered and concentrated in vacuo. The products are separated by preparative TLC on silica gel affording 4″-N-ethyl-aminomethyl-avermectin B1a/B1b characterized by $^1$H NMR and mass spectral analysis.

EXAMPLE 19

4″-Aminomethyl-avermectin B1a/B1b

To a stirred solution of 4″-exomethylene-avermectin B1a/B1b-4″,4″a-oxide (50 mg.) in methanol (2 mL.) is added a saturated solution of ammonia in methanol (0.5 mL.) and the mixture is stirred for 16 hours at 0° C. The reaction is diluted with water and extracted 4 times with methylene chloride. The organic extracts are combined, dried over anhydrous sodium sulfate, filtered and concentrated in vacuo. The products are separated by preparative TLC on silica gel affording 4″-aminomethyl-avermectin B1a/B1b characterized by $^1$H NMR and mass spectral analysis.

EXAMPLE 20

4″-N-Acetyl-aminomethyl-avermectin B1a/B1b

To a stirred solution of 4″-aminomethyl-avermectin B1a/B1b (16 mg.) in methylene chloride (0.20 mL.) is added a solution of acetic anhydride in $CH_2Cl_2$ (0.020 mL. 10% solution). The mixture is stirred for 1 h, then diluted with saturated aqueous sodium bicarbonate and extracted 4 times with methylene chloride. The organic extracts are combined, dried over anhydrous sodium sulfate, filtered, concentrated in vacuo and separated by preparative TLC on silica gel affording 4″-N-acetyl-aminomethyl-avermectin B1a/B1b characterized by 1H NMR and mass spectral analysis.

EXAMPLE 21

4″-Hydroxymethyl-avermectin B1a/B1b

To a stirred solution of 4″-exomethylene-avermectin B1a/B1b-4″,4″a-oxide (50 mg.) in tetrahydrofuran (3 mL.) is added aqueous perchloric acid (0.5 mL., 3N) and the mixture stirred for 1 hour at 0° C. The reaction is quenched by careful addition of saturated aqueous sodium bicarbonate and extracted 4 times with methylene chloride. The organic extracts are combined, dried over anhydrous sodium sulfate, filtered and concentrated in vacuo. The products are separated by preparative TLC on silica gel affording 4″-hydroxymethyl-avermectin B1a/B1b characterized by $^1$H NMR and mass spectral analysis.

What is claimed is:

1. A compound having the formula

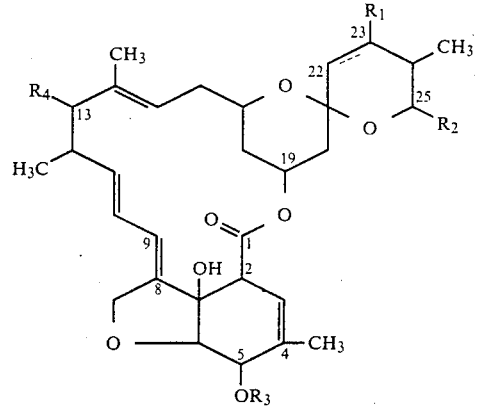

wherein the broken line at the 22,23 position represents a single bond and wherein $R_1$ is hydrogen or hydroxy or oxo, or the broken line represents a double bond and $R_1$ is absent;

$R_2$ is methyl, ethyl, or an alpha-branched $C_3$–$C_8$ alkyl or alkenyl group;

$R_3$ is hydrogen, loweralkyl or loweralkanoyl;

$R_4$ is

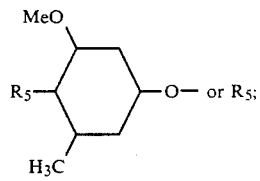

$R_5$ is

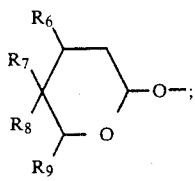

R₆ is hydrogen or loweralkoxy;
R₇ is halomethyl, phenylthiomethyl, hydroxymethyl, loweralkoxymethyl, loweralkanoyloxymethyl, aminomethyl, N-loweralkylaminomethyl, N,N-diloweralkylaminomethyl or loweralkanoylaminomethyl; and
R₈ is hydroxy; or
R₇ and R₈ together are methylene, or —CH₂O—;
R₉ is loweralkyl.

2. A compound of claim 1 wherein the broken line at the 22,23 position represents a single bond and wherein R₁ is hydrogen or hydroxy or oxo, or the broken line represents a double bond and R₁ is absent;
R₂ is iso-propyl, sec-butyl, or an alpha-branched C₃-C₈ alkenyl group;
R₃ is hydrogen;
R₄ is

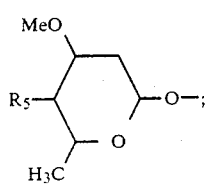

R₅ is

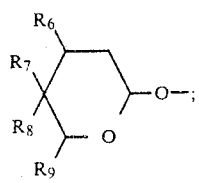

R₆ is hydrogen or methoxy:
R₇ is iodomethyl, phenylthiomethyl, hydroxymethyl, loweralkoxymethyl, loweralkanoyloxymethyl, aminomethyl, N-loweralkylaminomethyl, N,N-diloweralkylaminomethyl or loweralkanoylaminomethyl; and
R₈ is hydroxy; or
R₇ and R₈ together are methylene, or —CH₂O—;
R₉ is methyl.

3. A compound of claim 1 wherein the broken line at the 22,23 position represents a single bond and wherein R₁ is hydrogen or hydroxy or oxo, or the broken line represents a double bond and R₁ is absent;
R₂ is iso-propyl, sec-butyl, or an alpha-branched C₃-C₆ alkenyl group;
R₃ is hydrogen;
R₄ is

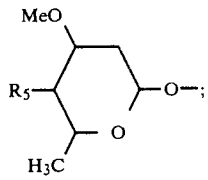

R₅ is

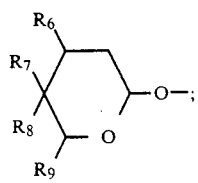

R₆ is hydrogen or methoxy;
R₇ is iodomethyl, phenylthiomethyl, hydroxymethyl, loweralkoxymethyl, loweralkanoyloxymethyl, aminomethyl, N-loweralkylaminomethyl, N,N-diloweralkylaminomethyl or loweralkanoylaminomethyl; and
R₈ is hydroxy; or
R₇ and R₈ together are methylene, or —CH₂O—;
R₉ is methyl.

4. A compound of claim 1 which is 4″-exomethylene-avermectin B1b-4″,4″a-oxide.

5. A compound of claim 1 which is 4″-deoxiy 4″-exomethylene-avermectin B1a/B1b.

6. A compound of claim 1 which is 4″-iodomethyl-avermectin B1a/B1b.

7. A compound of claim 1 which is 4″-phenylthiomethyl-avermectin B1a/B1b.

8. A compound of claim 1 which is 22,23-dihydro-4″-exomethylene-avermectin B1a/B1b-4″,4″a-oxide.

9. A method for the treatment of parasitic diseases of animals which comprises administering to said animal infected with parasites, an effective amount of a compound of claim 1.

10. A method for the treatment of parasitic diseases of plants which comprises administering to said plant infected with parasites, an effective amount of a compound of claim 1.

11. A composition useful for the treatment of parasitic diseases of plants or animals which comprises an inert carrier and an effective amount of a compound of claim 1.

* * * * *